US010201445B2

(12) United States Patent
Weber et al.

(10) Patent No.: US 10,201,445 B2
(45) Date of Patent: Feb. 12, 2019

(54) SELF-EXPANDING STENT DELIVERY SYSTEM

(71) Applicant: BOSTON SCIENTIFIC SCIMED, INC., Maple Grove, MN (US)

(72) Inventors: Jan Weber, Maastricht (NL); James M. Anderson, Corcoran, MN (US); Timothy A. Ostroot, Cokato, MN (US); Derek C. Sutermeister, Ham Lake, MN (US); Cass A. Hanson, St. Paul, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 566 days.

(21) Appl. No.: 14/666,250

(22) Filed: Mar. 23, 2015

(65) Prior Publication Data
US 2015/0265445 A1  Sep. 24, 2015

Related U.S. Application Data

(60) Provisional application No. 61/969,610, filed on Mar. 24, 2014.

(51) Int. Cl.
*A61F 2/966* (2013.01)
*A61F 2/95* (2013.01)
*A61F 2/958* (2013.01)

(52) U.S. Cl.
CPC .............. *A61F 2/966* (2013.01); *A61F 2/958* (2013.01); *A61F 2002/9517* (2013.01)

(58) Field of Classification Search
CPC .. A61F 2/966; A61F 2/95; A61F 2/954; A61F 2/958; A61F 2/962; A61F 2002/9517
See application file for complete search history.

(56) References Cited

U.S. PATENT DOCUMENTS

| | | | | |
|---|---|---|---|---|
| 5,201,757 A | * | 4/1993 | Heyn | A61F 2/95 606/198 |
| 5,238,004 A | | 8/1993 | Sahatjian et al. | |
| 5,919,204 A | * | 7/1999 | Lukic | A61F 2/95 606/198 |
| 6,059,813 A | | 5/2000 | Vrba et al. | |
| 6,413,269 B1 | * | 7/2002 | Bui | A61F 2/962 623/1.11 |

(Continued)

FOREIGN PATENT DOCUMENTS

| | | |
|---|---|---|
| EP | 1759668 A2 | 3/2007 |
| WO | 9415549 A1 | 7/1994 |
| WO | 2014014923 A1 | 1/2014 |

OTHER PUBLICATIONS

Chinese Office Action dated Aug. 3, 2017 from Chinese Patent Application No. 201580027225.9.

*Primary Examiner* — Ryan J Severson
*Assistant Examiner* — Christian Knauss
(74) *Attorney, Agent, or Firm* — Seager, Tufte & Wickhem, LLP

(57) ABSTRACT

Systems for the delivery of endoluminal devices are disclosed. An illustrative system may include a delivery sheath having an inner sheath and an outer sheath. The delivery sheath may be configured to restrain a stent in a compressed delivery configuration. The outer sheath may cover the entire length of the stent and the inner sheath may cover a portion of the length of the stent.

8 Claims, 12 Drawing Sheets

(56) References Cited

U.S. PATENT DOCUMENTS

| | | |
|---|---|---|
| 6,508,803 B1 | 1/2003 | Horikawa et al. |
| 6,544,278 B1 | 4/2003 | Vrba et al. |
| 7,175,650 B2 | 2/2007 | Ruetsch |
| 7,285,130 B2 | 10/2007 | Austin |
| 7,309,349 B2 | 12/2007 | Jackson et al. |
| 7,794,487 B2 | 9/2010 | Majercak et al. |
| 2002/0188341 A1 | 12/2002 | Elliott |
| 2003/0144671 A1 | 7/2003 | Brooks et al. |
| 2003/0176910 A1 | 9/2003 | Vrba et al. |
| 2007/0055340 A1* | 3/2007 | Pryor .................. A61F 2/95 623/1.11 |
| 2008/0208209 A1 | 8/2008 | Fischer et al. |
| 2008/0288042 A1 | 11/2008 | Purdy et al. |
| 2009/0099636 A1 | 4/2009 | Chandusko et al. |
| 2011/0118817 A1 | 5/2011 | Gunderson et al. |
| 2011/0152996 A1* | 6/2011 | Acosta ................. A61F 2/915 623/1.11 |
| 2013/0131775 A1* | 5/2013 | Hadley ................. A61F 2/966 623/1.11 |
| 2013/0317592 A1 | 11/2013 | Wuebbeling et al. |
| 2013/0345788 A1 | 12/2013 | Chandusko et al. |

\* cited by examiner

SELF-EXPANDING STENT DELIVERY SYSTEM

CROSS-REFERENCE TO RELATED APPLICATIONS

This application claims priority under 35 U.S.C. § 119 to U.S. Provisional Application Ser. No. 61/969,610 filed Mar. 24, 2014, the entirety of which is incorporated herein by reference.

TECHNICAL FIELD

The invention generally pertains to delivery systems for intraluminal devices.

BACKGROUND

A wide variety of intracorporeal medical devices have been developed for medical use, for example, intravascular use. Some of these devices include stents, guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices

SUMMARY

The disclosure is directed to several alternative designs, materials and methods of manufacturing medical device structures and assemblies.

In one example, a stent delivery system may comprise an elongate catheter shaft having a distal end region and a proximal end region. A stent having a proximal end region, a distal end region, and a length extending therebetween may be disposed about the distal end region of the elongate catheter shaft. A delivery sheath may be disposed over the elongate catheter shaft and the stent. The delivery sheath may comprise an outer sheath having a proximal end region and a distal end region. The outer sheath may further include a sliding element extending inwardly from an inner surface of the outer sheath. The delivery sheath may further include an inner sheath slidably disposed within the outer sheath. The inner sheath may have a proximal end region, a distal end region, and an axial slit extending along a portion of a length of the inner sheath. A solid lubricant disposed between the inner sheath and the outer sheath.

In another example, a stent delivery system may comprise an elongate catheter shaft having a distal end region and a proximal end region. A stent having a proximal end region, a distal end region, and a length extending therebetween may be disposed about the distal end region of the elongate catheter shaft. The stent delivery system may further comprise a handle including a thumb wheel, a pinion, and a rack assembly. The stent delivery system may further comprise a delivery sheath having a proximal end region and a distal end region. The proximal end region of the delivery sheath may be affixed to the rack assembly. The delivery sheath may be disposed over the elongate catheter shaft and the stent. The delivery sheath may comprise an outer sheath having a proximal end region and a distal end region. The delivery sheath may further include an inner sheath slidably disposed within the outer sheath. The inner sheath may have a proximal end region and a distal end region. A solid lubricant may be disposed between the inner sheath and the outer sheath.

In another example, a method for delivering a stent to a desired location may comprise providing a stent delivery system. The stent delivery system may comprise an elongate catheter shaft having a distal end region and a proximal end region. A stent having a proximal end region, a distal end region, and a length extending therebetween may be disposed about the distal end region of the elongate catheter shaft. The stent delivery system may further comprise a delivery sheath disposed over the elongate catheter shaft and the stent. The delivery sheath may comprise an outer sheath having a proximal end region and a distal end region, wherein the entire length of the stent is disposed within the outer sheath. The delivery sheath may further comprise an inner sheath slidably disposed within the outer sheath. The inner sheath may have a proximal end region and a distal end region, wherein the distal end region of the inner sheath is proximal to the distal end region of the stent. A solid lubricant may be disposed between the inner sheath and the outer sheath. The method for delivering the stent may further comprise advancing the stent delivery system to the desired location. The outer sheath may then be proximally retracted independently of the inner sheath over a distal portion of the stent. The outer sheath and the inner sheath may then be proximally retracted simultaneously over a proximal portion of the stent.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The invention may be more completely understood in consideration of the following detailed description of various embodiments in connection with the accompanying drawings, in which.

Figure 1:
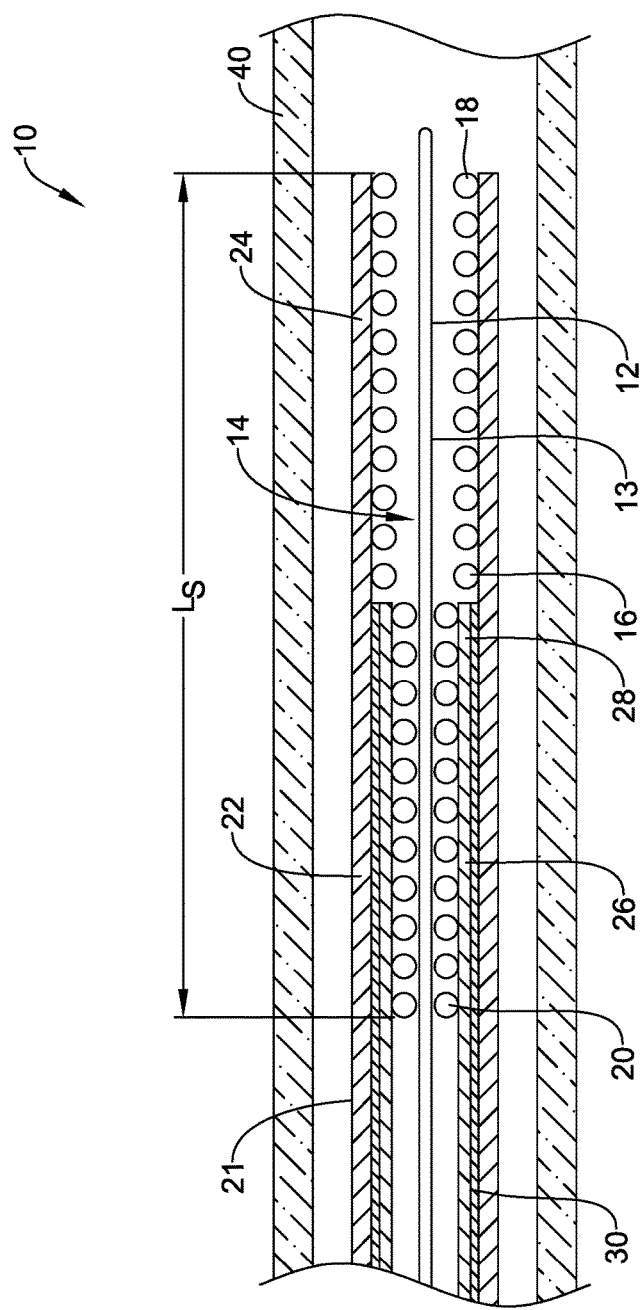
FIG. 1 is a cross-section of a distal end region of an illustrative stent delivery system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

To help prevent arterial closure, repair dissection, or prevent restenosis, a physician can implant an intravascular prosthesis, or a stent, for maintaining vascular patency inside an artery or other vessel at the lesion. Stents are also used for a variety of other purposes including maintaining the patency of any physiological conduit including but not limited to arteries, veins, vessels, the biliary tree, the urinary tract, the alimentary tract, the tracheobronchial tree, the genitourinary system, and the cerebral aqueduct. While many of the devices and methods described herein are discussed relative stent delivery systems, it is contemplated that the devices and methods may be used in other treatment locations and/or applications where intraluminal devices are desired. For example, the devices and methods may also be applicable to self-expanding trans-aorta valvular implant (TAVI) devices.

For the purposes of this disclosure stents and medical devices may be considered to include any stent, covered stent or prosthesis or any medical device system, grafts or biologic device.

In a stent deployment system which utilizes a retractable sheath, retraction of the sheath may result in inaccurate placement of the stent for a variety of reasons including, but not limited to, the interaction of the sheath and guide catheter or stent upon retraction. For example, during deployment (and loading) of self-expanding (SE) stents into a delivery sheath high frictional forces may occur between the stent surface and the sheath material. The longer the stent, the higher the overall shear force is that has to be overcome. These high shear forces may be especially damaging in relation to coated SE stents.

The irregular pattern of a compressed stent against the inner wall of a sheath may not form the most ideal situation to achieve the lowest possible friction forces. These "surfaces" may not be optimized for low sliding forces. The overall frictional force ($F_1$) occurring during the refraction of the sheath is the product of the sliding surface area times the normal frictional force per area. In an alternative delivery system, this force may be reduced by utilizing two sliding surfaces, each approximately half the original area. One sliding surface may be an area between the stent and the delivery sheath resulting in first friction force $F_2$, while the other sliding surface may be optimized just for sliding, using solid graphite lubrication or, for example, another lubrication, resulting in a second friction force $F_3$. Instead of a system having a total frictional force being $F_1$, the alternative delivery system may include two forces $F_2$ and $F_3$, whereby $F_2$ is approximately half $F_1$ by the fact that the area is half, and a second sliding area, the other half, whereby friction force $F_3$ is much less than $F_2$. The sum of the frictional forces ($F_2+F_3$) in the system utilizing two sliding surfaces may therefore be less than the frictional force ($F_1$) in a system utilizing a single sliding surface.

Figure 2:
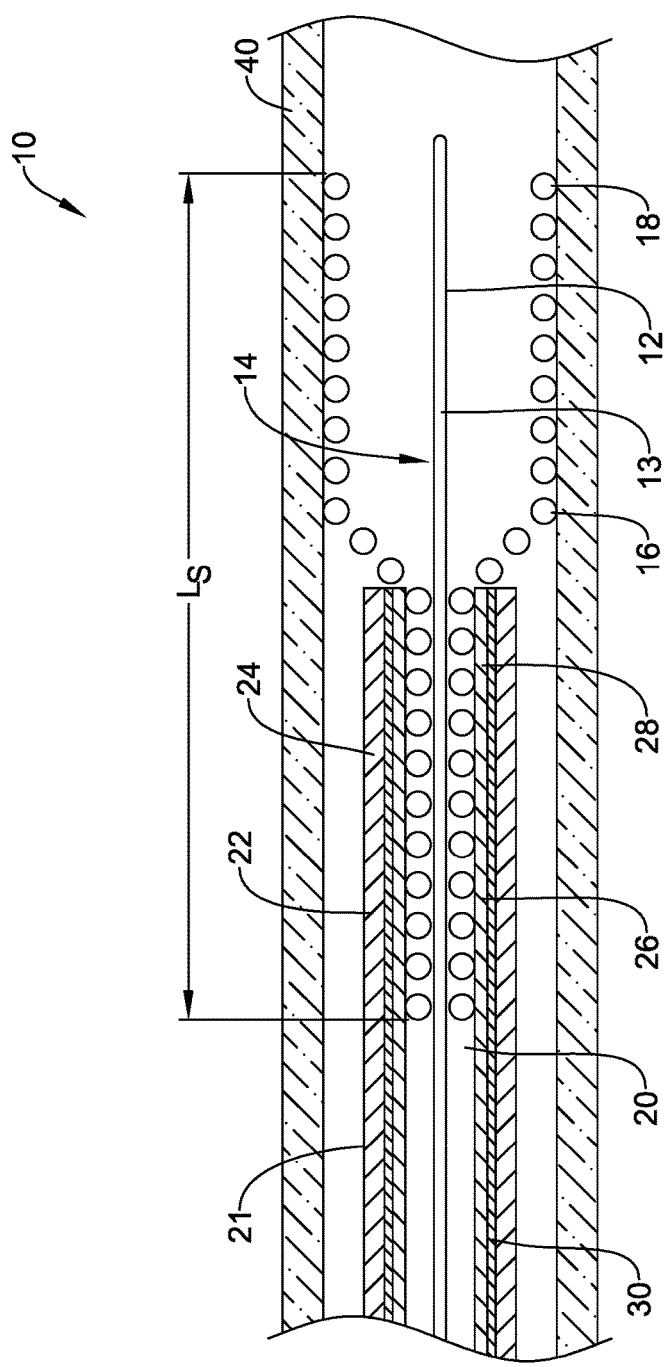
FIG. 2 is another cross-section of a distal end region of the illustrative stent delivery system of FIG. 1.
Figure 3:
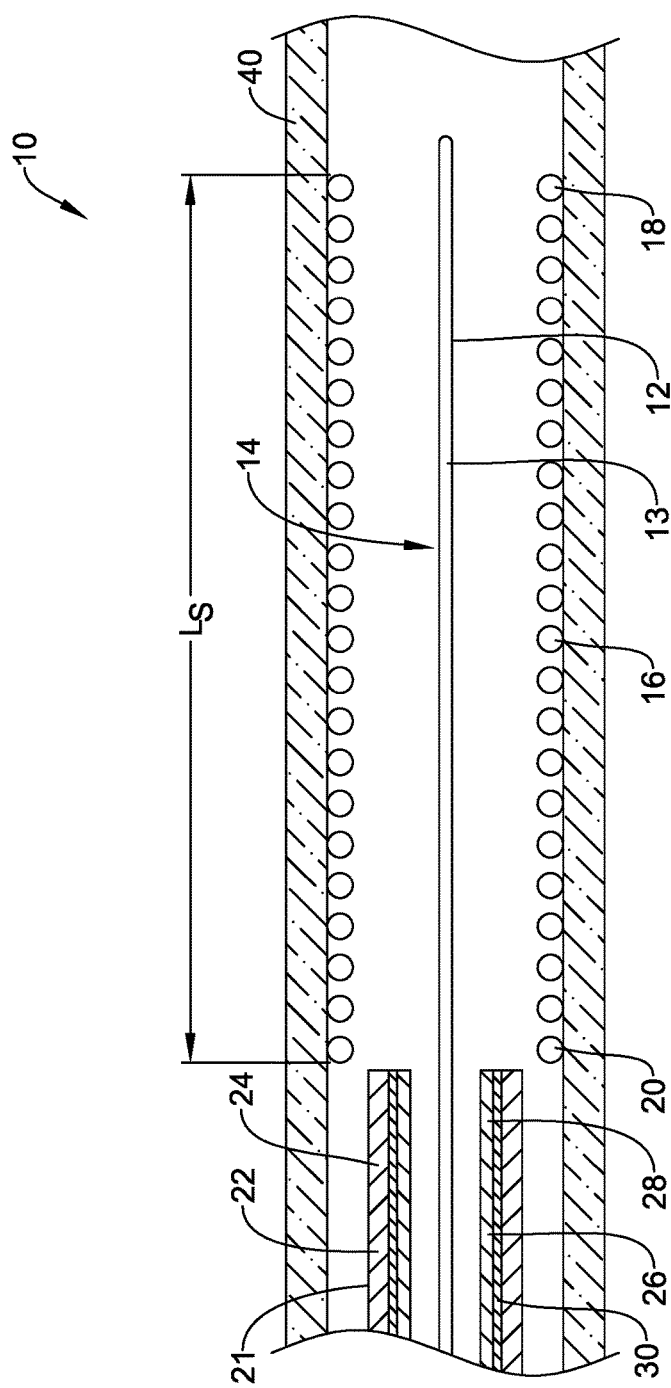
FIG. 3 is another cross-section of a distal end region of the illustrative stent delivery system of FIG. 1.

FIGS. 1-3 illustrate a cross-section of a distal portion of an illustrative stent delivery system 10 disposed within a body lumen 40. The delivery system 10 may include an elongate catheter shaft 12 having a proximal end (not shown) and a distal end region 14. The elongate shaft 12 may extend proximally from the distal end region 14 to the proximal end which is configured to remain outside of a patient's body. Although not shown, the proximal end of the elongate shaft 12 may include a hub attached thereto for connecting other treatment devices or providing a port for facilitating other treatments. It is contemplated that the stiffness and size of the elongate shaft 12 may be modified to form a delivery system 10 for use in various vessel diameters and various locations within the vascular tree. The catheter shaft 12 may further define a guidewire lumen 13 through which a guidewire (not explicitly shown) may be passed in order to advance the catheter to a predetermined position in a body lumen or vessel. Alternatively, the elongate shaft 12 may be configured as a push catheter without the need for guidewire and/or lumen 13.

A self-expanding stent 16 having a distal end region 18 and a proximal end region 20 may be disposed about the distal end region 14 of the elongate catheter shaft 12. The stent 16 may have a woven structure fabricated from a number of filaments. In some embodiments, the stent 16 may be braided with one filament. In other embodiments, the stent 16 may be braided with several filaments. In another embodiment, the stent 16 may be knitted. In yet another embodiment, the stent 16 may be of a knotted type. In still another embodiment, the stent 16 may be laser cut. In some embodiments the stent 16 may be at least partially constructed from a one or more of the following shape memory materials: nitinol, shape-memory polymer(s), FeMnSiCrNi shape-memory stainless steel, etc., but may include other material or materials as well. In some instances, the stent 16 may be constructed of regular metals but of a design which exhibits self-expansion characteristics. While the stent 16 is described as self-expanding, it is contemplated that the stent 16 may also be expanded using an expansion mechanism such as a balloon. In such an instance, the stent 16 may be delivered on an expandable balloon and the balloon used to expand the stent 16. In some embodiments the stent 16 may include one or more areas, bands, coatings, members etc. that is (are) detectable by imaging modalities such as X-Ray, MRI or ultrasound. In some embodiments, at least a portion of the stent 16 may be at least partially radiopaque. In some embodiments the stent 16 may include one or more therapeutic and/or lubricious coatings applied thereto. While the illustrative stent 16 is illustrated as having a relatively constant cross-sectional area in the expanded state, it is contemplated that the cross-sectional area of the stent 16 may vary from the proximal end region 20 to the distal end region 18. For example, the cross-sectional area may increase in size, or ramp, from the proximal end region 20 to the distal end region 18 or the cross-sectional area may decrease in size, or taper, from the proximal end region 20 to the distal end region 18. These are just examples. The size of the cross-sectional area of the stent 16 may vary in any manner desired.

In the various embodiments described herein the stent 16 is preferably configured to be at least partially self-expanding or have self-expanding characteristics. As used herein the term "self-expanding" refers to the tendency of the stent to return to a preprogrammed diameter when unrestrained from the catheter, such as in the manner depicted in FIG. 3. As shown in FIG. 1, when the stent 16 is disposed about the distal end region 14 of the elongate shaft 12, the stent 16 may be restrained in its reduced diameter or pre-delivery configuration by a retractable retaining or delivery sheath 21 which is disposed over the elongate shaft 12 and about the entire length of the stent 16 prior to delivery.

The delivery sheath 21 may have sufficient hoop strength to retain the stent 16 in its pre-delivery or reduced diameter state. The delivery sheath 21 may include an outer sheath 22 and an inner sheath 26 slidably disposed within the outer sheath 22. The inner sheath 26 and the outer sheath 22 may be configured to be proximally retracted independently from each other, simultaneously, or a combination thereof. In some instances, the outer surface of the inner sheath 26 may contact the inner surface of the outer sheath 22. In other instances, the outer surface of the inner sheath 26 may be spaced a distance from the inner surface of the outer sheath 22. For example, the inner sheath 26 may have an outer diameter that is smaller than or slightly smaller than an inner diameter of the outer sheath 22. This may result in a gap between the inner sheath 26 and the outer sheath 22 along the length of the inner sheath 26 where the stent 16 is not present while the stent 16 may exert an outward force on the inner sheath 26 such that the outer surface of the inner sheath 26 contacts the inner surface of the outer sheath 22 along the length of the inner sheath 26 disposed over the stent 16 (not explicitly shown). As such friction may occur only between the inner sheath 26 and the outer sheath 22 where there is an outward force created on the inner sheath 26 by the stent 16 disposed within the inner sheath 26.

In some embodiments, the outer sheath 22 may have a wall thickness that is greater than a wall thickness of the inner sheath 26 such that the outer sheath 22 may provide the structural rigidity of the delivery sheath 21. The outer sheath 22 may include a proximal end (not shown) and a distal end region 24. The outer sheath 22 may extend proximally from the distal end region 24 to the proximal end which may be configured to remain outside of a patient's body. Although not shown, the proximal end of the outer sheath 22 may include an actuation mechanism attached thereto which may be used to proximally retract or distally advance the delivery sheath 21. The distal end region 24 of the outer sheath 22 may be positioned such that the entire length $L_S$ of the stent 16 is disposed within the outer sheath 22 during delivery of the stent 16.

The inner sheath 26 may include a proximal end (not shown) and a distal end region 28. The inner sheath 26 may extend proximally from the distal end region 28 to the proximal end which may be configured to remain outside of a patient's body, although this is not required. In some instances, inner sheath 26 may have a length such that the proximal end of the inner sheath 26 may be positioned at a point between the proximal end of the catheter shaft 12 and the proximal end region 20 of the stent 16. In some embodiments, the inner sheath 26 and the outer sheath 22 may be attached to the same actuation mechanism or to separate actuation mechanisms. In other embodiments, only one of the inner sheath 26 or the outer sheath 22 may be affixed to an actuation mechanism.

The inner sheath 26 may extend over a portion of the length $L_S$ of the stent 16 such that the distal end region 28 of the inner sheath 26 is proximal to the distal end region 18 of the stent 16. For example, the inner sheath 26 may be disposed over greater than 90% of the length $L_S$ of the stent 16, in the range of 10-90% of the length $L_S$ of the stent 16, in the range of 25-75% of the length $L_S$ of the stent 16, in the range of 40-60% of the length $L_S$ of the stent 16, or less than 10% of the length $L_S$ of the stent 16. These are just examples. It is contemplated that the inner sheath 26 may be disposed over any portion of the length $L_S$ of the stent 16 desired.

In a system having only a single delivery sheath, the overall frictional force ($F_1$) occurring during the refraction of the sheath is the product of the sliding surface area times the normal frictional force per area. In the present embodiment, this force may be reduced by utilizing two sliding surfaces, each approximately half the original area. A first sliding surface may be present between the stent 16 and the outer sheath 22 and a second sliding surface between may be present the outer sheath 22 and the inner sheath 26. It is contemplated that the second sliding surface may be optimized for sliding or to minimize the frictional forces through the use of a lubricant or other friction reducing means. In the present embodiment, the first sliding surface may have a first frictional force, $F_2$, that is approximately half of frictional force $F_1$ as the area of the stent 16 the outer sheath 22 is traveling over has been reduced by half. The second sliding surface may have a second frictional force, $F_3$ which is significantly less than the first frictional force $F_2$ as the second sliding surface has been optimized to minimize friction. The sum of the frictional forces ($F_2+F_3$) in the current embodiment utilizing two sliding surfaces may therefore be less than the frictional force ($F_1$) in a system utilizing a single sliding surface to move the sheath the same distance.

In some instances, the inner sheath 26 may have a length that is approximately twice as long as the portion of the inner sheath 26 covering the stent 16. For example, if the inner sheath 26 is disposed over approximately 50% of the length $L_S$ of the stent 16, then the inner sheath 26 may have a length that is approximately equal to the length of the stent 16. This is just an example. It is contemplated that the inner sheath 26 may have any length desired.

FIG. 1 illustrates the distal end region 18 of the stent 16 disposed within the outer sheath 22 and the proximal end region 20 of the stent 16 disposed within the inner sheath 26 and the outer sheath 22. The tendency of the stent 16 to expand may cause the distal end region 18 of the stent 16 to have a larger cross-section than the proximal end region 20.

It is contemplated that the inner sheath 26 and the outer sheath 22 may be formed from the same materials or different materials, as desired. In some instances, the outer sheath 22 may be formed from a material that allows the outer sheath 22 to provide a radial inward force while also providing the desired longitudinal stiffness for advancing the delivery sheath 21 through the vasculature. For example, the outer sheath 22 may include an inner polymer layer, an intermediate braided layer, and an outer polymer layer. It is contemplated that the inner sheath 26 may only need to be "stiff" in a longitudinal sense to prevent the inner sheath 26 from buckling when the outer sheath 22 is proximally retracted over then inner sheath 26. In some embodiments, the inner sheath 26 may be formed from an ultrathin-wall hypotube to minimize wall thickness and to provide a smooth, flat inner and outer surface.

The delivery sheath 21 may further include a solid lubricant 30 disposed between the inner sheath 26 and the outer sheath 22 to minimize the frictional forces occurring between the inner sheath 26 and the outer sheath 22. In some instances, the solid lubricant 30 may be, graphene, graphene oxide, or oxinated graphene sheets having a coefficient of friction in the range of 0.01 to 0.05, although other lubricants may also be used. For example, tungsten-disulfide, a non-toxic and robust lubricant having a coefficient of friction in the range of 0.03 to 0.07, may also be used. It is contemplated that the sliding forces between monolayer graphene sheets may be extremely low. In some instances, the solid lubricant may remain in the desired location whereas a fluid lubricant may migrate during storage time. It is contemplated that one or more layers of the solid lubricant 30 may be disposed on an outer surface of the inner sheath 26, an inner surface of the outer sheath 22, positioned between the inner sheath 26 and the outer sheath 22, or any combination thereof.

While the lubricant 30 is described as a solid lubricant, it is contemplated that other lubricants may also be used. For example, the lubricant 30 may be a liquid lubricant or an embedded lubricant (for example, embedded in the inner sheath 26 or the outer sheath 22). It is further contemplated that the lubricant 30 may cross-linked with the inner sheath 26 and/or outer sheath 22 or may be adhered layers.

The stent delivery system 10 may be advanced to a desired treatment location while the delivery sheath 21 maintains the stent 16 in a collapsed position. Once the stent 16 is positioned adjacent to the target location, the outer sheath 22 may be proximally retracted independently of the inner sheath 26 over a distal portion of the stent 16 while the inner sheath 26 is kept stationary as shown in FIG. 2. As the outer sheath 22 is retracted, the overall or majority of the friction force may occur between the outer sheath 22 and the distal end region 18 of the stent 16. The sliding surface between the outer sheath 22 and the inner sheath 26 may be optimized such that the friction between the outer sheath 22 and the inner sheath 26 is negligible. Thus, if the inner sheath 26 covers approximately 50% of the length of the stent $L_S$, the frictional forces of retracting the outer sheath 22 from the delivery configuration, shown in FIG. 1, to the point where the distal end region 24 of the outer sheath 22 is generally aligned with the distal end region 28 of the inner sheath 26, shown in FIG. 2, is approximately half the frictional force of associated with the retraction of a single sheath over the same distance. Once the distal end region 24 of the outer sheath 22 is generally aligned with the distal end region 28 of the inner sheath 26, both the outer sheath 22 and the inner sheath 26 may be proximally retracted simultaneously over a proximal portion of the stent 16 to fully deploy the stent 16, as shown in FIG. 3. It is contemplated that the delivery system 10 may include stent retention features to restrict the stent 16 from moving proximally during retraction of the delivery sheath 21.

While the illustrative delivery sheath 21 is shown as including two sheaths, the outer sheath 22 and the inner sheath 26, it is contemplated that more than two sheaths may be used to form the delivery sheath 21. For example, the delivery sheath 21 may include two, three, four, or more concentrically disposed sheaths. The sheaths may include a solid lubricant disposed between each layer to reduce the friction between the layers. The layers may form an antenna-like or telescoping structure.

Figure 4A:
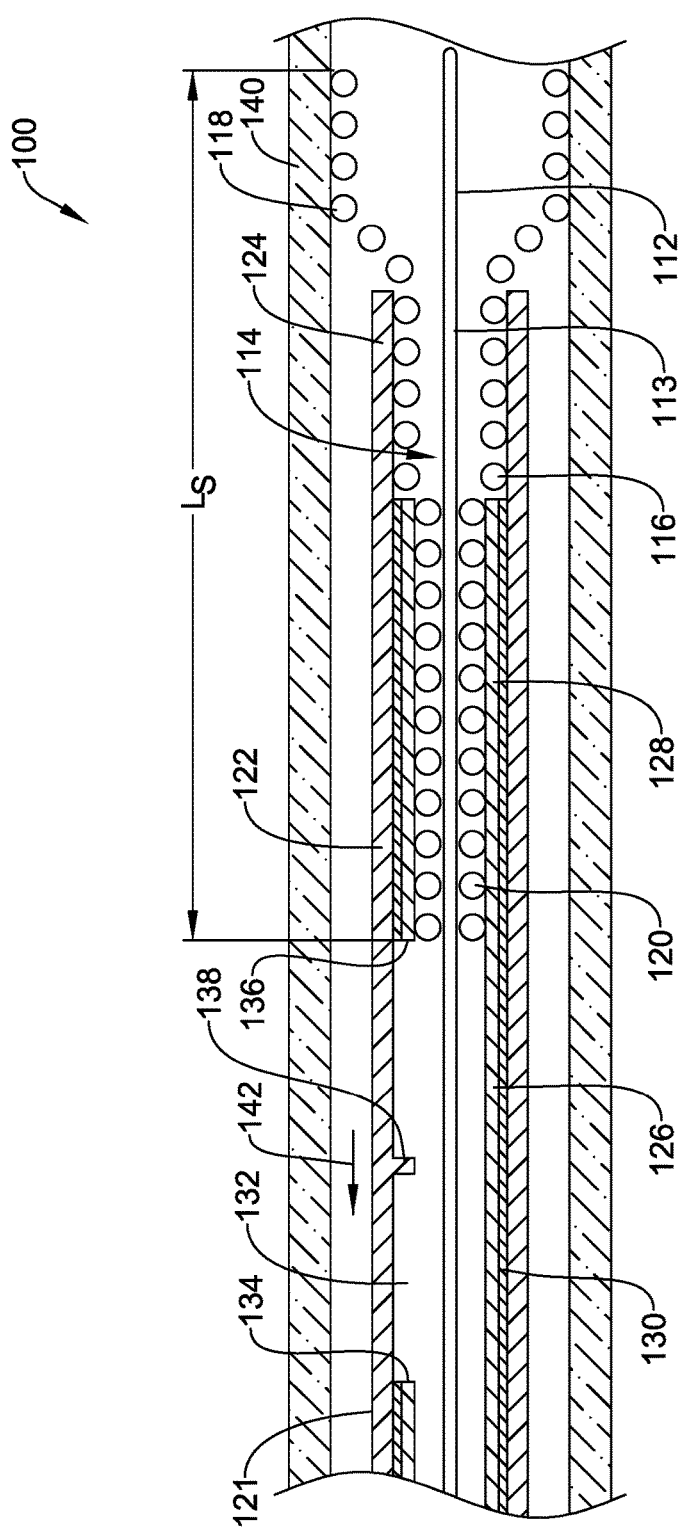
FIGS. 4A-4B are cross-sections of a distal end region of another illustrative stent delivery system.
Figure 4B:
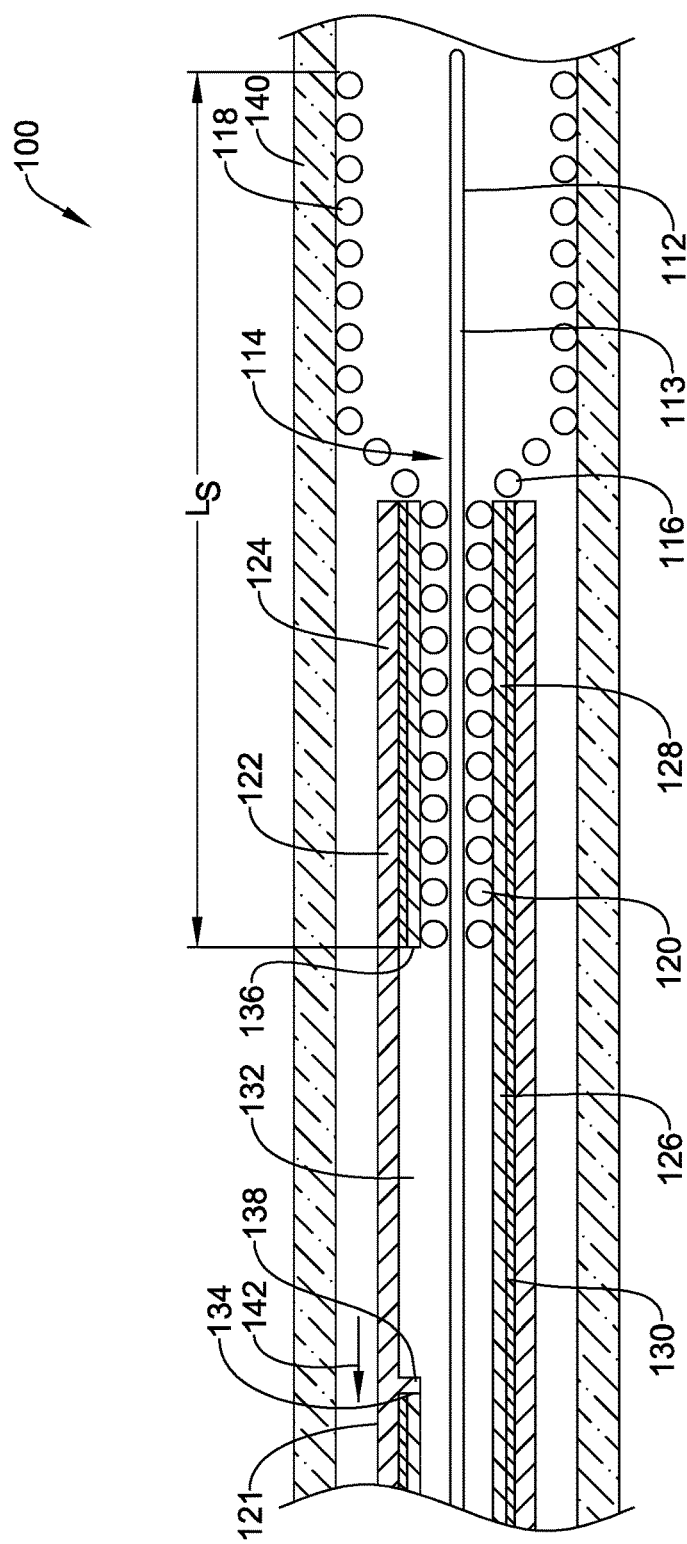

FIGS. 4A-4B illustrate a cross-section of a distal portion of another illustrative stent delivery system 100 disposed within a body lumen 140. Delivery system 100 may be similar in form and function to delivery system 10 described above. The delivery system 100 may include an elongate catheter shaft 112 having a proximal end (not shown) and a distal end region 114. The elongate shaft 112 may extend proximally from the distal end region 114 to the proximal end which is configured to remain outside of a patient's body. Although not shown, the proximal end of the elongate shaft 112 may include a hub attached thereto for connecting other treatment devices or providing a port for facilitating other treatments. It is contemplated that the stiffness and size of the elongate shaft 112 may be modified to form a delivery system 100 for use in various vessel diameters and various locations within the vascular tree. The catheter shaft 112 may further define a guidewire lumen 113 through which a guidewire (not explicitly shown) may be passed in order to advance the catheter to a predetermined position in a body lumen or vessel. Alternatively, the elongate shaft 112 may be configured as a push catheter without the need for guidewire and/or lumen 113.

A self-expanding stent 116 having a distal end region 118 and a proximal end region 120 may be disposed about the distal end region 114 of the elongate catheter shaft 112. The stent 116 may be similar in form and function to stent 16 described above. While the stent 116 is described as self-expanding, it is contemplated that the stent 116 may also be expanded using an expansion mechanism such as a balloon. In such an instance, the stent 116 may be delivered on an expandable balloon and the balloon used to expand the stent 116. In some embodiments the stent 116 may include one or more areas, bands, coatings, members etc. that is (are) detectable by imaging modalities such as X-Ray, MRI or ultrasound. In some embodiments, at least a portion of the stent 116 may be at least partially radiopaque. In some embodiments the stent 116 may include one or more therapeutic and/or lubricious coatings applied thereto.

When the stent 116 is disposed about the distal end region 114 of the elongate shaft 112, the stent 116 may be restrained in its reduced diameter or pre-delivery configuration by a retractable retaining or delivery sheath 121 which is disposed over the elongate shaft 112 and about the entire length of the stent 116 prior to delivery. In FIG. 4A, the delivery sheath 121 is shown as partially proximally retracted allowing the distal end region 118 of the stent 116 to expand to its preprogrammed diameter while the proximal end region 120 remains restrained in its reduced diameter configuration.

The delivery sheath 121 may have sufficient hoop strength to retain the stent 116 in its pre-delivery or reduced diameter state. The delivery sheath 121 may include an outer sheath 122 and an inner sheath 126 slidably disposed within the outer sheath 122. The inner sheath 126 and the outer sheath 122 may be configured to be proximally retracted independently from each other, simultaneously, or a combination thereof. In some instances, the outer surface of the inner sheath 126 may contact the inner surface of the outer sheath 122. In other instances, the outer surface of the inner sheath 126 may be spaced a distance from the inner surface of the outer sheath 122.

In some embodiments, the outer sheath 122 may have a wall thickness that is greater than a wall thickness of the inner sheath 126 such that the outer sheath 122 may provide the structural rigidity of the delivery sheath 121. The outer sheath 122 may include a proximal end (not shown) and a distal end region 124. The outer sheath 122 may extend proximally from the distal end region 124 to the proximal end which may be configured to remain outside of a patient's body. Although not shown, the proximal end of the outer sheath 122 may include an actuation mechanism attached thereto which may be used to proximally retract or distally advance the delivery sheath 121. The distal end region 124 of the outer sheath 122 may be positioned such that the entire length $L_S$ of the stent 116 is disposed within the outer sheath 122 during delivery of the stent 116.

The inner sheath 126 may include a proximal end (not shown) and a distal end region 128. The inner sheath 126 may extend proximally from the distal end region 128 to the proximal end which may be configured to remain outside of a patient's body, although this is not required. In some instances, inner sheath 126 may have a length such that the proximal end of the inner sheath 126 may be positioned at a point between the proximal end of the catheter shaft 112 and the proximal end region 120 of the stent 116. In some embodiments, the inner sheath 126 and the outer sheath 122 may be attached to the same actuation mechanism or to separate actuation mechanisms. In other embodiments, only one of the inner sheath 126 or the outer sheath 122 may be affixed to an actuation mechanism.

The inner sheath 126 may extend over a portion of the length $L_S$ of the stent 116 such that the distal end region 128 of the inner sheath 126 is proximal to the distal end region 118 of the stent 116. For example, the inner sheath 126 may be disposed over greater than 90% of the length $L_S$ of the stent 116, in the range of 10-90% of the length $L_S$ of the stent 116, in the range of 25-75% of the length $L_S$ of the stent 116, in the range of 40-60% of the length $L_S$ of the stent 116, or less than 10% of the length $L_S$ of the stent 116. These are just examples. It is contemplated that the inner sheath 126 may be disposed any portion of the length $L_S$ of the stent 116 desired.

In a system having only a single delivery sheath, the overall frictional force ($F_1$) occurring during the refraction of the sheath is the product of the sliding surface area times the normal frictional force per area. In the present embodiment, this force may be reduced by utilizing two sliding surfaces, each approximately half the original area. A first sliding surface may be present between the stent 116 and the outer sheath 122 and a second sliding surface between may be present the outer sheath 122 and the inner sheath 126. It is contemplated that the second sliding surface may be optimized for sliding or to minimize the frictional forces through the use of a lubricant or other friction reducing means. In the present embodiment, the first sliding surface may have a first frictional force, $F_2$, that is approximately half of frictional force $F_1$ as the area of the stent 116 the outer sheath 122 is traveling over has been reduced by half. The second sliding surface may have a second frictional force, $F_3$ which is significantly less than the first frictional force $F_2$ as the second sliding surface has been optimized to minimize friction. The sum of the frictional forces ($F_2+F_3$) in the current embodiment utilizing two sliding surfaces may therefore be less than the frictional force ($F_1$) in a system utilizing a single sliding surface to move the sheath the same distance.

In some instances, the inner sheath 126 may have a length that is approximately twice as long as the portion of the inner sheath 126 covering the stent 116. For example, if the inner sheath 126 is disposed over approximately 50% of the length $L_S$ of the stent 116, then the inner sheath 126 may have a length that is approximately equal to the length of the stent 116. This is just an example. It is contemplated that the inner sheath 126 may have any length desired.

It is contemplated that the inner sheath 126 and the outer sheath 122 may be formed from the same materials or different materials as desired. In some instances, the outer sheath 122 may be formed from a material that allows the outer sheath 122 to provide a radial inward force while also providing the desired longitudinal stiffness for advancing the delivery sheath 121 through the vasculature. For example, the outer sheath 122 may include an inner polymer layer, an intermediate braided layer, and an outer polymer layer. It is contemplated that the inner sheath 126 may only need to be "stiff" in a longitudinal sense to prevent the inner sheath 126 from buckling when the outer sheath 122 is proximally retracted over then inner sheath 126. In some embodiments, the inner sheath 126 may be formed from an ultrathin-wall hypotube to minimized wall thickness and to provide a smooth, flat inner and outer surface. The delivery sheath 121 may further include a solid lubricant 130 disposed between the inner sheath 126 and the outer sheath 122. In some instances, the solid lubricant 130 may be oxinated graphene sheets having a coefficient of friction in the range of 0.01 to 0.05. It is contemplated that the sliding forces between monolayer graphene sheets may be extremely low. In some instances, the solid lubricant may remain in the desired location whereas a fluid lubricant may migrate during storage time. It is contemplated that one or more layers of the solid lubricant 130 may be disposed on an outer surface of the inner sheath 126, an inner surface of the outer sheath 122, positioned between the inner sheath 126 and the outer sheath 122, or any combination thereof.

The inner sheath 126 may include one or more axial slits or slots 132 extending along a portion of a length of the inner sheath 126. The axial slit 132 may extend from an outer surface towards an inner surface of the inner sheath 126. In some embodiments, the axial slit 132 may only extend partially through the wall of the inner sheath 126. In other embodiments, the axial slit 132 may extend through the entire wall of the inner sheath. The slit 132 may have a proximal end 134 distal to the proximal end region of the inner sheath 126 and a distal end 136 proximal to the distal end region 128 of the inner sheath 126. In some instances, the distal end 136 of the slit 132 may be proximal to or adjacent to the proximal end region 120 of the stent 116. While the inner sheath 126 is illustrated as including a single axial slit 132, it is contemplated that the inner sheath 126 may include any number of slits 132 desired, such as, but not limited to, one, two, three, four, or more. The slits 132 may be arranged about the circumference of the inner sheath 126 in any manner desired. In some embodiments, the slits 132 may be evenly spaced about the circumference. In other embodiments, the slits 132 may be grouped together or otherwise asymmetrically arranged.

The outer sheath 122 may include one or more sliding elements 138 extending inwardly from the inner surface of the outer sheath 122. The one or more sliding elements 138 may be configured to engage the one or more axial slits 132 in the inner sheath 126. It is contemplated that the sliding element 138 may be a pin, protrusion, rod, dowel, or other element capable of extending into or otherwise engaging slit 132. While the outer sheath 122 is illustrated as including a single sliding element 138, it is contemplated that the outer sheath 122 may include any number of sliding elements 138 desired, such as, but not limited to, one, two, three, four, or more. It is contemplated that each sliding element 138 provided may engage a corresponding axial slit 132 in the inner sheath 126. Accordingly, the sliding elements 138 may be positioned to generally align with a corresponding slit 132. In some embodiments, the sliding element 138 may be formed as a unitary structure with the outer sheath 122. In other embodiments, the sliding element 138 may be formed as a separate structure from the outer sheath 122 and subsequently attached to the outer sheath. It is contemplated that the sliding element 138 may be attached to the outer sheath 122 in any number of ways, such as, but not limited to: adhesive bonding, hot melt bonding, friction bonding, etc.

The stent delivery system 100 may be advanced to a desired treatment location while the delivery sheath 121 maintains the stent 116 in a collapsed position. While FIG. 4A illustrates the stent 116 as partially deployed, it should be understood the stent 116 is advanced to the desired treatment location fully within the delivery sheath 121. Once the stent 116 is positioned adjacent to the target location, the outer sheath 122 may be proximally retracted independently of the inner sheath 126 over a distal portion of the stent 116 while the inner sheath 126 is kept stationary. It is contemplated that the outer sheath 122 may be actuated through any number of actuation mechanisms, such as, but not limited to: knobs, levers, thumbwheels, etc. As the outer sheath 122 is proximally retracted, the sliding element 138 may move proximally within the axial slit 132 as shown at arrow 142. Further proximal refraction of the outer sheath 122 may cause the sliding element 138 to engage a mating feature or the proximal end 134 of the axial slit 132 as shown in FIG. 4B. The length of the slit 132 may be selected such that distal end region 124 of the outer sheath 122 can be retracted to generally align with the distal end region 128 of the inner sheath 126 prior to or at the same time as the sliding element 138 engaging the proximal end 134 of the slit 132. For example, the length of the slit 132 may be approximately equal to the length of the stent 116 that is not disposed within the inner sheath 126. Once the sliding element has engaged the proximal end 134 of the axial slit 132, further proximal retraction of the outer sheath 122 may pull the inner sheath 126 with the outer sheath 122 to fully deploy the stent 116 such that the outer sheath 122 and the inner sheath 126 are simultaneously retracted over a distal portion of the stent 116. It is contemplated that the delivery system 100 may include stent retention features to restrict the stent 116 from moving proximally during retraction of the delivery sheath 121.

While the illustrative delivery sheath 121 is shown as including two sheaths, the outer sheath 122 and the inner sheath 126, it is contemplated that more than two sheaths may be used to form the delivery sheath 121. For example, the delivery sheath 121 may include two, three, four, or more concentrically disposed sheaths. The sheaths may include a solid lubricant disposed between each layer to reduce the friction between the layers. It is contemplated that the layers may be connected to one another through a series of sliding elements and slits. The layers may form an antenna-like or telescoping structure.

Figure 5A:
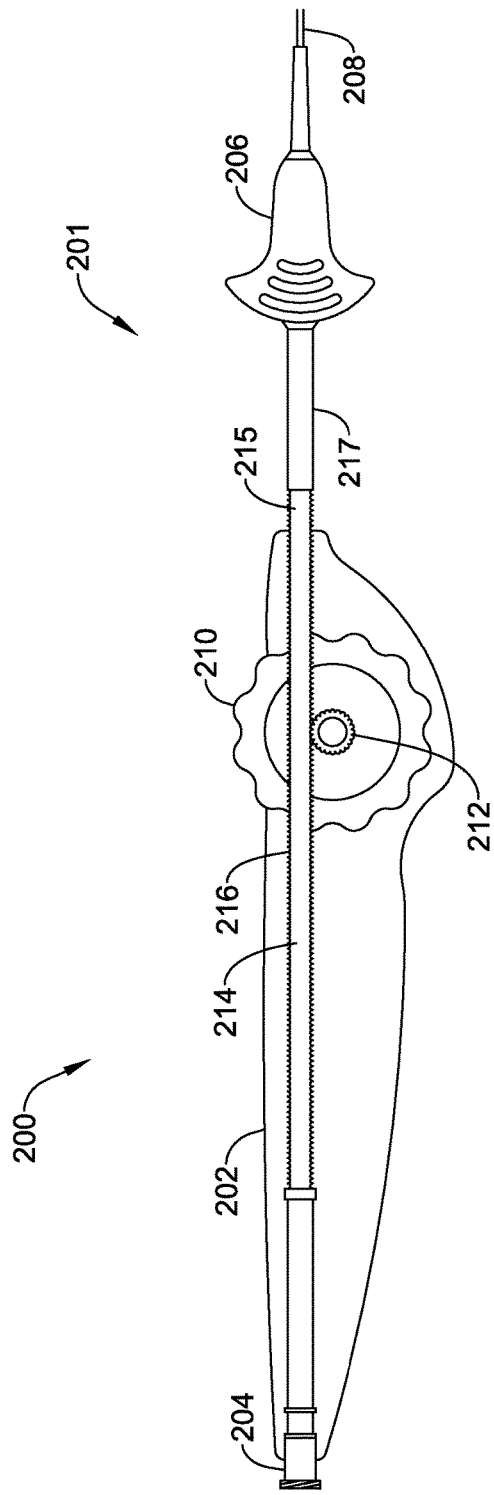
FIGS. 5A-5C are cross-sections of a proximal end region of another illustrative stent delivery system.

FIG. 5A illustrates a proximal end region 201 of another illustrative stent delivery system 200 in partial cross-section. The proximal end region 201 of the stent delivery system 200 may include a handle body 202 configured to remain outside the body. The handle body 202 may include a Luer fitting 204 at a proximal end thereof. The handle body 202 may further include a two-stage rack assembly 215. A distal end region 217 of the rack assembly 215 may be affixed to a pull grip 206 and a delivery sheath 208. The delivery sheath 208 may be similar in form and function to delivery sheaths 21, 121 described above and will be described in more detail below. The handle body 202 may further include a thumb wheel 210. The thumb wheel 210 may be manipulated by an operator to drive a pinion 212. The pinion 212 may include gear teeth 213 (see FIGS. 5B and 5C) configured to engage corresponding teeth and grooves 216, 230 on the rack assembly 215. Rotation of the thumb wheel 210 may rotate the pinion 212 causing longitudinal movement of the rack assembly 215. While not explicitly shown, the handle 202 may include features such as a safety lock or a pawl to prevent or reduce unintentional movement or to limit the direction of movement of the rack assembly 215.

Figure 5B:
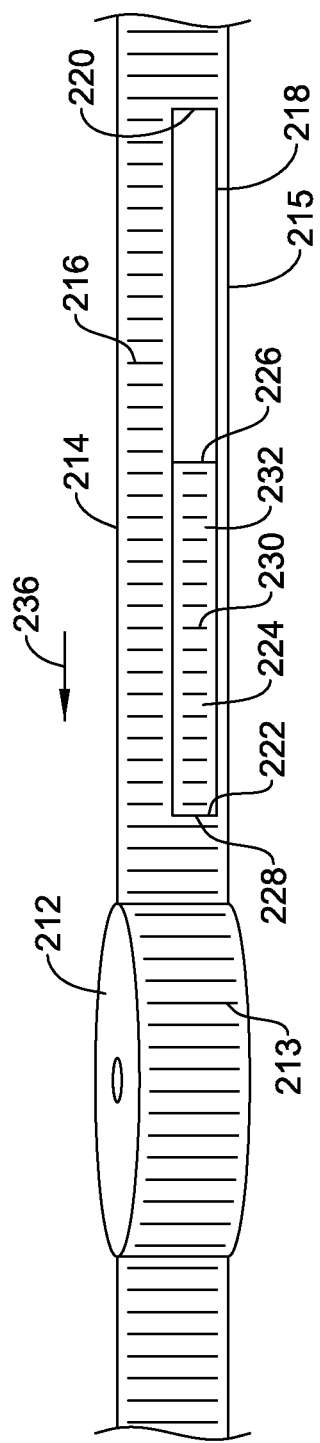
Figure 5C:
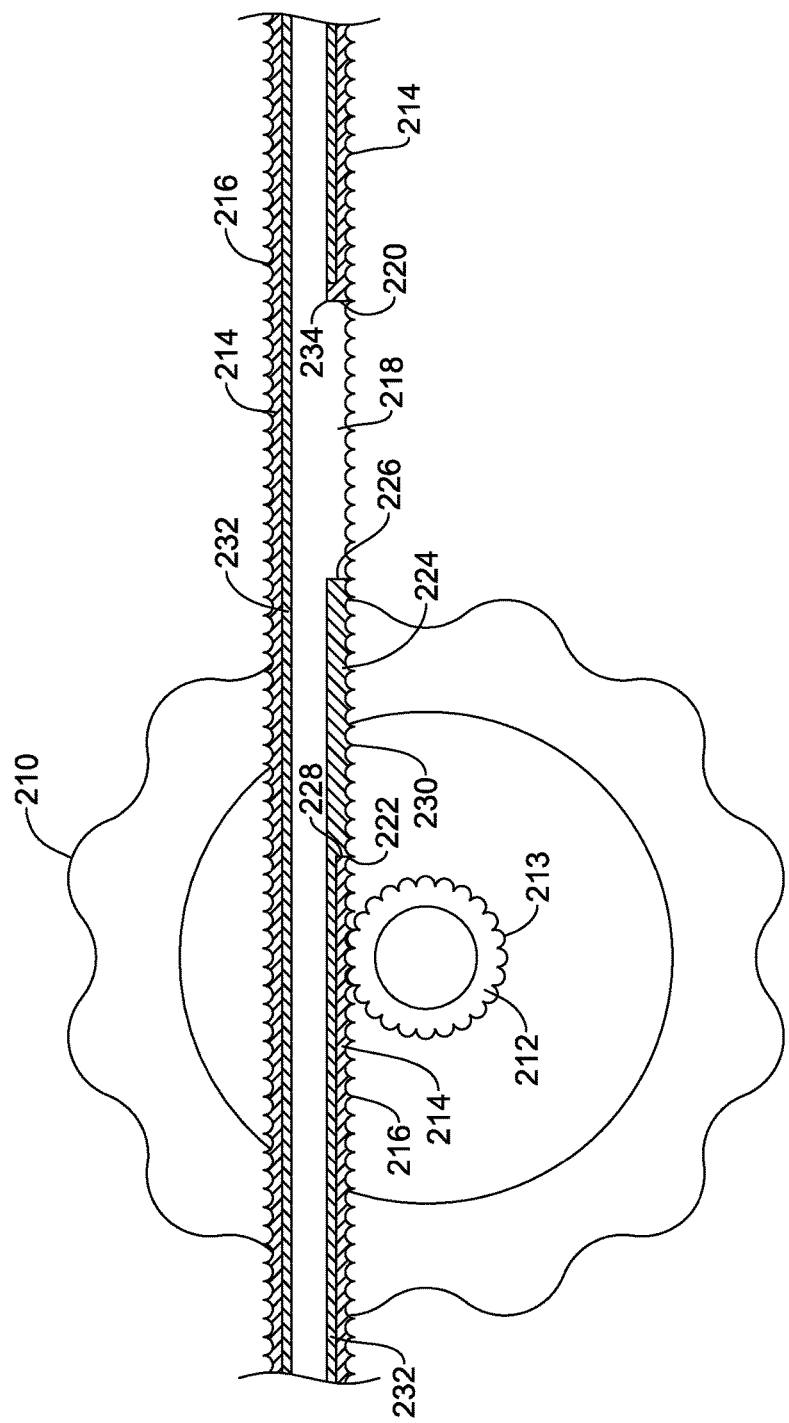

Referring now to FIG. 5B which illustrates a top view of the pinion 212 and rack assembly 215 and FIG. 5C which illustrates an enlarged cross-sectional view of the thumb wheel 210, pinion 212, and rack assembly 215. The rack assembly 215 may include an outer tubular member 214 and an inner tubular member 232. The inner tubular member 232 may be concentrically disposed within the outer tubular member 214. The inner tubular member 232 may be slidably disposed within the outer tubular member 214 such that the outer tubular member 214 and the inner tubular member 232 can be moved independently. In some instances, the outer surface of the inner tubular member 232 may contact the inner surface of the outer tubular member 214. In other instances, the outer surface of the inner tubular member 232 may be spaced a distance from the inner surface of the outer tubular member 214.

The outer tubular member 214 may include a plurality of teeth and grooves 216 configured to engage the teeth 213 on the pinion 212. The outer tubular member 214 may further include a slot 218 extending from a proximal end 222 to a distal end 220. The outer tubular member 214 may include a protrusion or pushing element 234 disposed adjacent the distal end 220 of the slot 218. As will be discussed in more detail below, the pushing element 234 may engage a portion of the inner tubular member 232. A region 224 of the inner tubular member 232 having a proximal end 228 and a distal end 226 may extend through the slot 218. Region 224 may include a plurality of teeth and grooves 230 configured to engage the teeth 213 of the pinion 212. The region 224 may have a thickness such that the teeth and grooves 230 on the inner tubular member 232 generally radially align with the teeth and grooves 216 on the outer tubular member 214. In some instances, the wall thickness of the inner tubular member 232 at region 224 may be thicker than the wall thickness of the remaining inner tubular member 232.

Figure 6A:
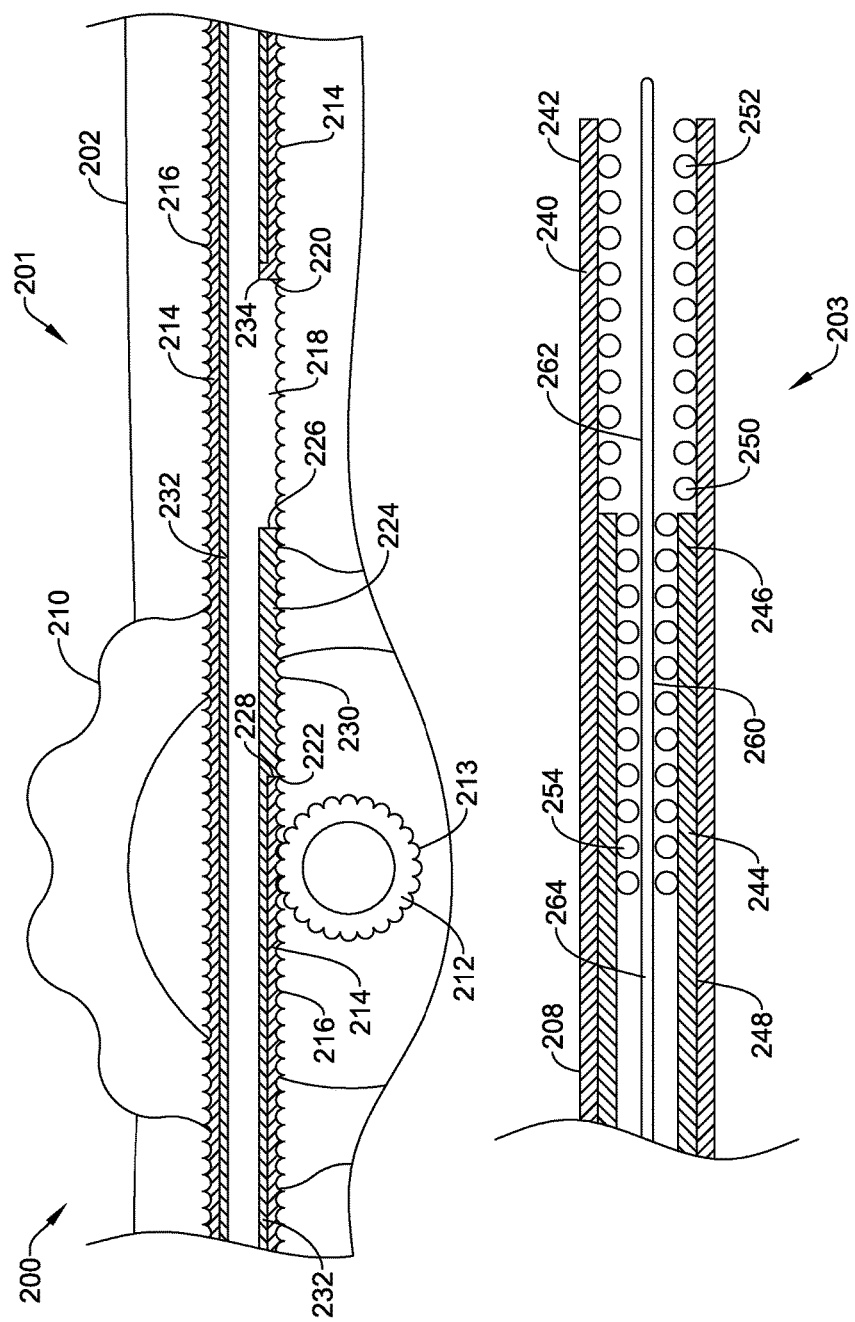
FIGS. 6A-6C are cross-sections of the illustrative stent delivery system of FIGS. 5A-5C.
Figure 6B:
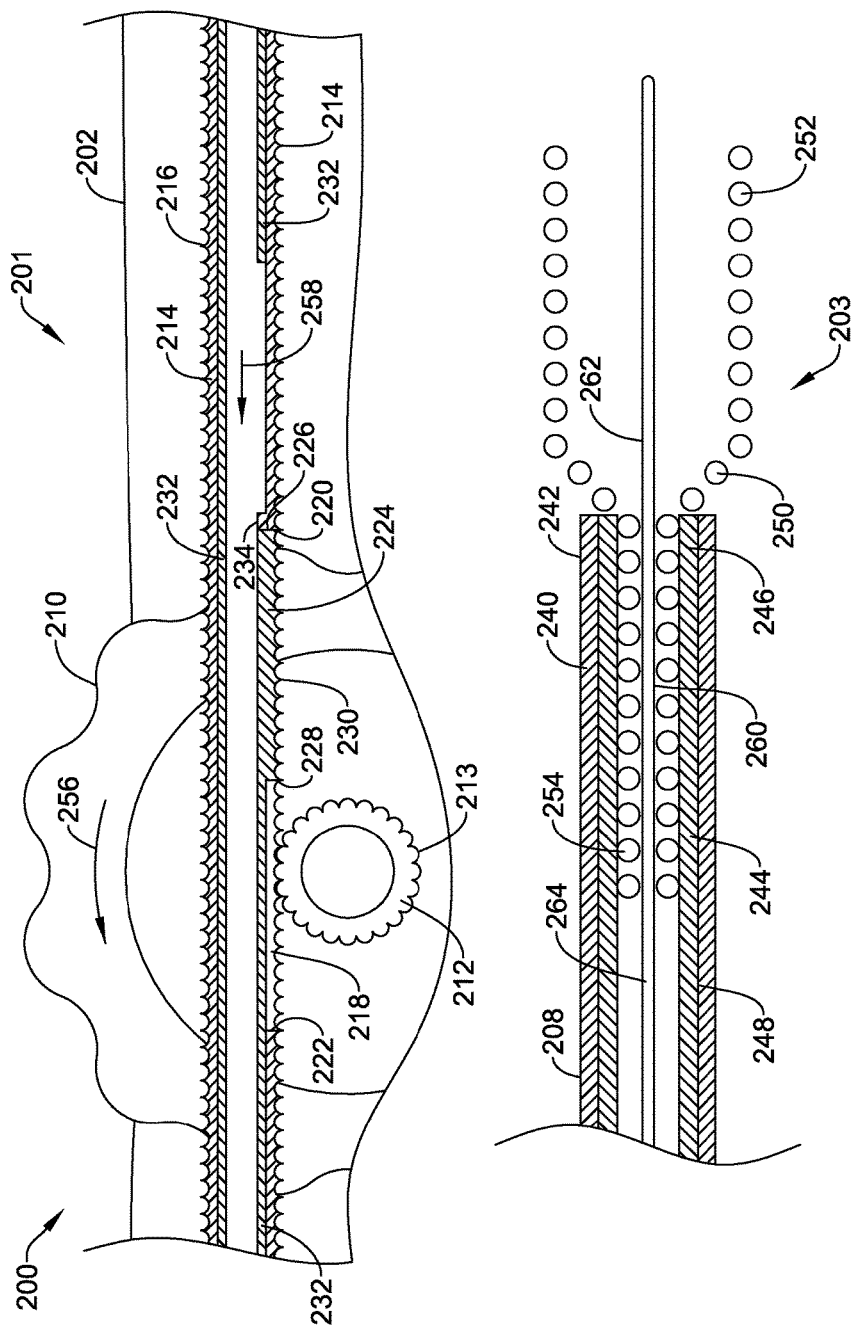
Figure 6C:
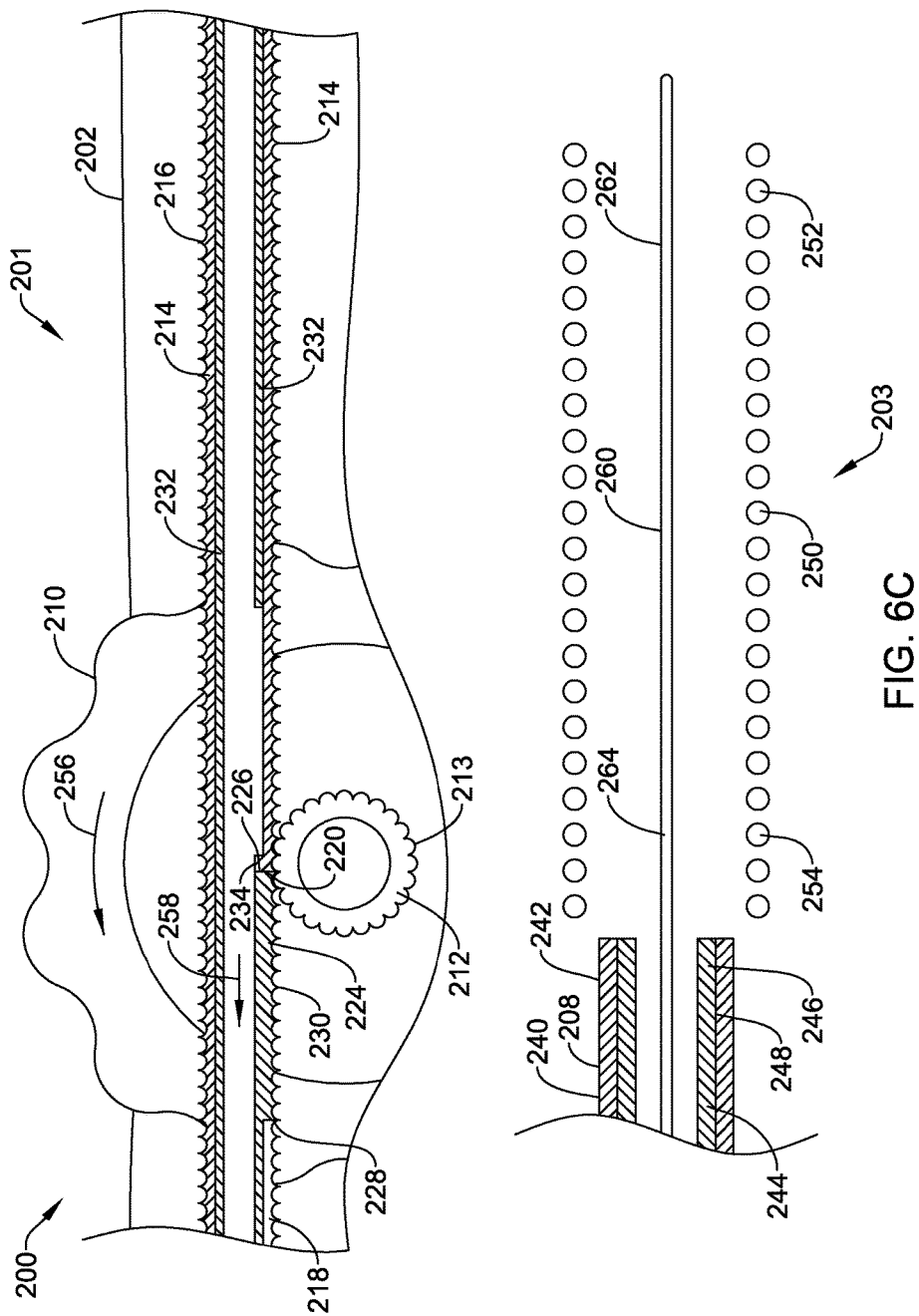

FIGS. 6A-6C illustrate another cross-section the illustrative stent delivery system 200 including the proximal end region 201 and a distal end region 203. Delivery system 200 may be similar in form and function to delivery systems 10, 100 described above. The delivery system 200 may include an elongate catheter shaft 260 having a proximal end (not shown) and a distal end region 262. The elongate shaft 260 may extend proximally from the distal end region 262 to the proximal end which is configured to remain outside of a patient's body. Although not shown, the proximal end of the elongate shaft 260 may include a hub attached thereto for connecting other treatment devices or providing a port for facilitating other treatments. It is contemplated that the stiffness and size of the elongate shaft 260 may be modified to form a delivery system 200 for use in various vessel diameters and various locations within the vascular tree. The catheter shaft 260 may further define a guidewire lumen 264 through which a guidewire (not explicitly shown) may be passed in order to advance the catheter to a predetermined position in a body lumen or vessel. Alternatively, the shaft elongate 260 may be configured as a push catheter without the need for guidewire and/or lumen 264.

A self-expanding stent 250 having a distal end region 252 and a proximal end region 254 may be disposed about the distal end region 262 of the elongate catheter shaft 260. The stent 250 may be similar in form and function to stents 16, 116 described above. While the stent 250 is described as self-expanding, it is contemplated that the stent 250 may also be expanded using an expansion mechanism such as a balloon. In such an instance, the stent 250 may be delivered on an expandable balloon and the balloon used to expand the stent 250. In some embodiments the stent 250 may include one or more areas, bands, coatings, members etc. that is (are) detectable by imaging modalities such as X-Ray, MRI or ultrasound. In some embodiments, at least a portion of the stent 250 may be at least partially radiopaque. In some embodiments the stent 250 may include one or more therapeutic and/or lubricious coatings applied thereto.

When the stent 250 is disposed about the distal end region 262 of the elongate shaft 260, the stent 250 may be restrained in its reduced diameter or pre-delivery configuration by a retractable retaining or delivery sheath 208 which is disposed over the elongate shaft 260 and about the entire length of the stent 250 prior to delivery. The delivery sheath 208 may have sufficient hoop strength to retain the stent 250 in its pre-delivery or reduced diameter state. The delivery sheath 208 may include an outer sheath 240 and an inner sheath 244 slidably disposed within the outer sheath 240. The inner sheath 244 and the outer sheath 240 may be configured to be proximally retracted independently from each other, simultaneously, or a combination thereof. In some embodiments, the outer sheath 240 may have a wall thickness that is greater than a wall thickness of the inner sheath 244 such that the outer sheath 240 may provide the structural rigidity of the delivery sheath 208. The outer sheath 240 may include a proximal end (not shown) and a distal end region 242. The outer sheath 240 may extend proximally from the distal end region 242 to the proximal end which may be configured to remain outside of a patient's body. The proximal end of the outer sheath 240 may be fixedly secured to the outer tubular member 214 of the rack assembly 215 such that longitudinal movement of the outer tubular member 214 is translated to the outer sheath 240. The distal end region 242 of the outer sheath 240 may be positioned such that the entire length of the stent 250 is disposed within the outer sheath 240 during delivery of the stent 250.

The inner sheath 244 may include a proximal end (not shown) and a distal end region 246. The inner sheath 244 may extend proximally from the distal end region 246 to the proximal end which may be configured to remain outside of a patient's body, although this is not required. The proximal end of the inner sheath 244 may be fixedly secured to the inner tubular member 232 of the rack assembly 215 such that longitudinal movement of the inner tubular member 232 is translated to the inner sheath 244. In some embodiments, the inner sheath 244 may extend over the entire length of the stent 250 or only a portion of the length of the stent 250. The inner sheath 244 may extend over a portion of the length of the stent 250 such that the distal end region 246 of the inner sheath 244 is proximal to the distal end region 252 of the stent 250.

It is contemplated that the inner sheath 244 and the outer sheath 240 may be formed from the same materials or different materials as desired. In some instances, the outer sheath 240 may be formed from a material that allows the outer sheath 240 to provide a radial inward force while also providing the desired longitudinal stiffness for advancing the delivery sheath 208 through the vasculature. For example, the outer sheath 240 may include an inner polymer layer, an intermediate braided layer, and an outer polymer layer. It is contemplated that the inner sheath 244 may only need to be "stiff" in a longitudinal sense to prevent the inner sheath 244 from buckling when the outer sheath 240 is proximally retracted over then inner sheath 244. In some embodiments, the inner sheath 244 may be formed from an ultrathin-wall hypotube to minimized wall thickness and to provide a smooth, flat inner and outer surface. The delivery sheath 208 may further include a solid lubricant 248 disposed between the inner sheath 244 and the outer sheath 240. In some instances, the solid lubricant 248 may be oxinated graphene sheets having a coefficient of friction in the range of 0.01 to 0.05. It is contemplated that the sliding forces between monolayer graphene sheets may be extremely low. In some instances, the solid lubricant may remain in the desired location whereas a fluid lubricant may migrate during storage time. It is contemplated that one or more layers of the solid lubricant 248 may be disposed on an outer surface of the inner sheath 244, an inner surface of the outer sheath 240, positioned between the inner sheath 244 and the outer sheath 240, or any combination thereof.

In a system having only a single delivery sheath, the overall frictional force ($F_1$) occurring during the refraction of the sheath is the product of the sliding surface area times the normal frictional force per area. In the present embodiment, this force may be reduced by utilizing two sliding surfaces, each approximately half the original area. A first sliding surface may be present between the stent 250 and the outer sheath 240 and a second sliding surface between may be present the outer sheath 240 and the inner sheath 244. It is contemplated that the second sliding surface may be optimized for sliding or to minimize the frictional forces through the use of a lubricant or other friction reducing means. In the present embodiment, the first sliding surface may have a first frictional force, $F_2$, that is approximately half of frictional force $F_1$ as the area of the stent 250 the outer sheath 240 is traveling over has been reduced by half. The second sliding surface may have a second frictional force, $F_3$ which is significantly less than the first frictional force $F_2$ as the second sliding surface has been optimized to minimize friction. The sum of the frictional forces ($F_2+F_3$) in the current embodiment utilizing two sliding surfaces may therefore be less than the frictional force ($F_1$) in a system utilizing a single sliding surface to move the sheath the same distance.

The stent delivery system 200 may be advanced to a desired treatment location while the delivery sheath 208 maintains the stent 250 in a collapsed position. Once the stent 250 is positioned adjacent to the target location, the outer sheath 240 may be proximally retracted independently of the inner sheath 244 over a distal portion of the stent 250 while the inner sheath 244 is kept stationary. For example, an operator may rotate the thumb wheel 210 in the direction shown by arrow 256 in FIG. 6B. Rotation of the thumb wheel 210 may also cause pinion 212 to rotate. As the teeth 213 on the pinion 212 engage the teeth and grooves 216 on the outer tubular member 214, the outer tubular member 214 may slide proximally in the direction of arrow 258. While the outer tubular member 214 is moved proximally over a first distance due to the initial rotation of the thumb wheel 210 and pinion 212, the inner tubular member 232 may remain stationary. The independent movement of the outer tubular member 214, and thus the independent movement of the outer sheath 240, may be a first stage of the two-stage rail. As the outer tubular member 214 continues to move proximally, the distal end 220 of the slot 218 and the pushing element 234 may approach the distal end 226 of the enlarged region 224 of the inner tubular member 232. The length of the slot 218 may be selected such that distal end region 242 of the outer sheath 240 can be refracted to generally align with the distal end region 246 of the inner sheath 244 prior to or at the same time as the pushing element 234 engaging the distal end 226 of the enlarged region 224 of the inner tubular member 232. For example, the length of the slot 218 may be approximately equal to the length of the stent 250 that is not disposed within the inner sheath 244.

The proximal movement of the outer tubular member 214 is translated to the outer sheath 240. As the outer sheath 240 is proximally retracted the stent 250 begins to expand and deploy. Further rotation of the thumb wheel 210 and thus further proximal retraction of the outer tubular member 214 may cause the pushing element 234 to engage the distal end 226 of the enlarged region 224 of the inner tubular member 232 as shown in FIG. 6B. Once the pushing element 234 has engaged the distal end 226 of the enlarged region 224 of the inner tubular member 232, further proximal retraction of the outer tubular member 214 may pull the inner tubular member 232 to the pinion 212 such that the teeth and grooves 230 on the inner tubular member 232 engage the teeth 213 on the pinion 212. Further rotation of the thumb wheel 210 may then cause simultaneous proximal movement of both the outer tubular member 214 and the inner tubular member 232 over a second distance, as shown in FIG. 6C. The simultaneous movement of the outer tubular member 214 and the inner tubular member 232, and thus the simultaneous movement of the outer sheath 240 and the inner sheath 244, may be a second stage of the two-stage rail. The proximal movement of the outer tubular member 214 and the inner tubular member 232 may be translated to the outer sheath 240 and the inner sheath 244 such that the outer sheath 240 and the inner sheath 244 are proximally retracted simultaneously over a proximal portion of the stent 250 to fully deploy the stent 250, as shown in FIG. 6C. It is contemplated that the delivery system 200 may include stent retention features to restrict the stent 250 from moving proximally during retraction of the delivery sheath 208.

While the illustrative delivery sheath 208 is shown as including two sheaths, the outer sheath 240 and the inner sheath 244, it is contemplated that more than two sheaths may be used to form the delivery sheath 208. For example, the delivery sheath 208 may include two, three, four, or more concentrically disposed sheaths. The sheaths may include a solid lubricant disposed between each layer to reduce the friction between the layers. It is contemplated that the layers may be connected to one another through a series of sliding elements and slits. The layers may form an antenna-like or telescoping structure.

Figure 7:
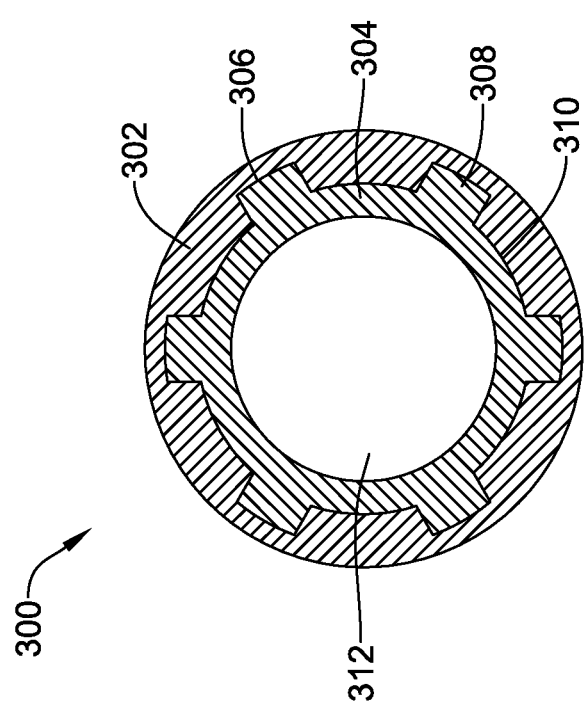
FIG. 7 is a cross-section of an illustrative delivery sheath.

FIG. 7 illustrates a cross-section of in illustrative delivery sheath 300 including an outer sheath 302 and an inner sheath. The outer sheath 302 may include a plurality of grooves 306 configured to a plurality of protrusions 308 on the inner sheath 304. This may create a grooved interlock between the outer sheath 302 and the inner sheath 304 which may reduce the profile of the delivery sheath 300 while also increasing pushability. The delivery sheath 300 may further include a solid lubricant 310 disposed between the inner sheath 304 and the outer sheath 302 to minimize the frictional forces occurring between the inner sheath 304 and the outer sheath 302. In some instances, the solid lubricant 310 may be oxinated graphene sheets having a coefficient of friction in the range of 0.01 to 0.05, although other lubricants may also be used. It is contemplated that the sliding forces between monolayer graphene sheets may be extremely low. In some instances, the solid lubricant may remain in the desired location whereas a fluid lubricant may migrate during storage time. It is contemplated that one or more layers of the solid lubricant 310 may be disposed on an outer surface of the inner sheath 304, an inner surface of the outer sheath 302, positioned between the inner sheath 304 and the outer sheath 302, or any combination thereof. The delivery sheath 300 may further include a lumen 312 for receiving an elongate catheter shaft and/or stent.

The materials that can be used for the various components of systems 10, 100, 200, 300 (and/or other systems disclosed herein) may include those commonly associated with medical devices. For simplicity purposes, the following discussion makes reference to sheath 21. However, this is not intended to limit the systems and methods described herein, as the discussion may be applied to other components in systems 10, 100, 200, 300.

Sheath 21 and/or other components of systems 10, 100, 200, 300 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of system 10, 100, 200, 300 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of systems 10, 100, 200, 300 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of system 10, 100, 200, 300 to achieve the same result.

In some embodiments, a degree of Magnetic Resonance Imaging (MRI) compatibility is imparted into systems 10, 100, 200, 300. For example, sheath 21 or portions thereof, may be made of a material that does not substantially distort the image and create substantial artifacts (i.e., gaps in the image). Certain ferromagnetic materials, for example, may not be suitable because they may create artifacts in an MRI image. Sheath 21 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be suitable for use in system 100 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

ADDITIONAL EXAMPLES

In a first example, a stent delivery system may comprise an elongate catheter shaft having a distal end region and a proximal end region, a stent having a proximal end region, a distal end region, and a length extending therebetween, the stent disposed about the distal end region of the elongate catheter shaft, and a delivery sheath disposed over the elongate catheter shaft and the stent, the delivery sheath comprising: an outer sheath having a proximal end region, a distal end region, and a sliding element extending inwardly from an inner surface of the outer sheath, an inner sheath slidably disposed within the outer sheath, the inner sheath having a proximal end region, a distal end region, and an axial slit extending along a portion of a length of the inner sheath, and a solid lubricant disposed between the inner sheath and the outer sheath.

Alternatively, or in addition, and in a second example, the sliding element of the first example may be configured to extend into the axial slit.

Alternatively, or in addition, and in a third example, the distal end region of the inner sheath of any of the first or second examples may be proximal to the distal end region of the stent.

Alternatively, or in addition, and in a fourth example, the entire length of the stent of any of the first through third examples may be disposed within the outer sheath.

Alternatively, or in addition, and in a fifth example, the inner sheath of any of the first through fourth examples may be disposed over in the range of 40-60% of the length of the stent.

Alternatively, or in addition, and in a sixth example, the outer sheath of any of the first through fifth examples may be configured to be proximally retracted independently of the inner sheath over a distal portion of the stent and simultaneously with the inner sheath over a proximal portion of the stent.

Alternatively, or in addition, and in a seventh example, the solid lubricant of any of the first through sixth examples may comprise graphene sheets.

Alternatively, or in addition, and in an eighth example, a stent delivery system may comprise an elongate catheter shaft having a distal end region and a proximal end region, a stent having a proximal end region, a distal end region, and a length extending therebetween, the stent disposed about the distal end region of the elongate catheter shaft, a handle including a thumb wheel, a pinion, and a rack assembly, and a delivery sheath having a proximal end region and distal end region, the proximal end region affixed to the rack assembly, wherein the delivery sheath is disposed over the elongate catheter shaft and the stent, the delivery sheath comprising: an outer sheath having a proximal end region and a distal end region, an inner sheath slidably disposed within the outer sheath, the inner sheath having a proximal end region and a distal end region, and a solid lubricant disposed between the inner sheath and the outer sheath.

Alternatively, or in addition, and in a ninth example, the rack assembly of the eighth example may comprise an outer tubular member and an inner tubular member slidably disposed within the outer tubular member.

Alternatively, or in addition, and in a tenth example, the outer tubular member of the ninth example may include a slot extending from an outer surface to an inner surface of the outer tubular member, the slot having a proximal end, a distal end, and a pushing element disposed adjacent the distal end.

Alternatively, or in addition, and in an eleventh example, the inner tubular member of the ninth or tenth example may include an enlarged region having a proximal end and a distal end, the enlarged region configured to extend into the slot of the outer tubular member.

Alternatively, or in addition, and in a twelfth example, rotation of the thumb wheel of any of the ninth through eleventh examples may be configured to proximally retract the outer tubular member independently of the inner tubular member over a first distance.

Alternatively, or in addition, and in a thirteenth example, further rotation of the thumb wheel of the twelfth example may be configured to proximally retract the outer tubular member and the inner tubular member simultaneously over a second distance.

Alternatively, or in addition, and in a fourteenth example, the inner sheath of any of the eighth through thirteenth examples may be disposed over in the range of 40-60% of the length of the stent.

Alternatively, or in addition, and in a fifteenth example, the solid lubricant of any of the eighth through fourteenth examples may comprise graphene sheets.

Alternatively, or in addition, and in a sixteenth example, a method for delivering a stent to a desired location may comprise providing a stent delivery system, the stent delivery system comprising: an elongate catheter shaft having a distal end region and a proximal end region, a stent having a proximal end region, a distal end region, and a length extending therebetween, the stent disposed about the distal end region of the elongate catheter shaft, and a delivery sheath disposed over the elongate catheter shaft and the stent, the delivery sheath comprising: an outer sheath having a proximal end region and a distal end region, wherein the entire length of the stent is disposed within the outer sheath, an inner sheath slidably disposed within the outer sheath, the inner sheath having a proximal end region and a distal end region, wherein the distal end region of the inner sheath is proximal to the distal end region of the stent, and a solid lubricant disposed between the inner sheath and the outer sheath, advancing the stent delivery system to the desired location, proximally retracting the outer sheath independently of the inner sheath over a distal portion of the stent, and proximally retracting the outer sheath and the inner sheath simultaneously over a proximal portion of the stent.

Alternatively, or in addition, and in a seventeenth example, proximally retracting the outer sheath of the sixteenth example independently of the inner sheath may comprise proximally retracting the outer sheath until a sliding element on the outer sheath engages a mating feature on the inner sheath.

Alternatively, or in addition, and in a eighteenth example, proximally retracting the outer sheath and the inner sheath of the sixteenth or seventeenth examples simultaneously over a proximal portion of the stent may comprise the sliding element pulling the inner sheath with the outer sheath.

Alternatively, or in addition, and in a nineteenth example, proximally retracting the outer sheath of the sixteenth example independently of the inner sheath over a distal portion of the stent may comprise rotating a thumb wheel in a first stage of a two stage rail system.

Alternatively, or in addition, and in a twentieth example, proximally retracting the outer sheath and the inner sheath of the sixteenth or nineteenth examples simultaneously over a proximal portion of the stent may comprise rotating a thumb wheel in a second stage of the two stage rail system.

What is claimed is:

1. A stent delivery system comprising:
  an elongate catheter shaft having a distal end region and a proximal end region; a stent having a proximal end region, a distal end region, and a length extending therebetween, the stent disposed about the distal end region of the elongate catheter shaft; and
  a delivery sheath disposed over the elongate catheter shaft and the stent, the delivery sheath comprising:
    an outer sheath extending at least partially over and surrounding the stent and having a proximal end region, a distal end region, and a sliding element extending inwardly from an inner surface of the outer sheath;
    an inner sheath extending at least partially over and surrounding the stent and slidably disposed radially within the outer sheath, the inner sheath having a proximal end region, a distal end region, and an axial slit extending from an outer surface towards an inner surface of the inner sheath and along a portion of a length of the inner sheath, the axial slit having a proximal end positioned distal to the proximal end region of the inner sheath and a distal end positioned proximal to the distal end region of the inner sheath;

wherein the sliding element is configured to extend into the axial slit;

wherein the outer sheath is configured to be proximally retracted independently of the inner sheath over a distal portion of the stent and simultaneously with the inner sheath over a proximal portion of the stent;

and a lubricant disposed between the inner sheath and the outer sheath.

2. The stent delivery system of claim 1, wherein the distal end region of the inner sheath is proximal to the distal end region of the stent.

3. The stent delivery system of claim 2, wherein the entire length of the stent is disposed within the outer sheath.

4. The stent delivery system of claim 2, wherein the inner sheath is disposed over in the range of 40-60% of the length of the stent.

5. The stent delivery system of claim 1, wherein the lubricant is a solid lubricant comprising graphene sheets.

6. A method for delivering a stent to a desired location comprising:

providing a stent delivery system, the stent delivery system comprising:

an elongate catheter shaft having a distal end region and a proximal end region;

a stent having a proximal end region, a distal end region, and a length extending therebetween, the stent disposed about the distal end region of the elongate catheter shaft; and a delivery sheath disposed over the elongate catheter shaft and the slant, the delivery sheath comprising:

an outer sheath having a proximal end region and a distal end region, and a sliding element extending inwardly from an inner surface of the outer sheath, wherein the entire length of the stent is disposed within the outer sheath:

an inner sheath slidably disposed radially within the outer sheath, the inner sheath having a proximal end region and a distal end region and an axial slit extending from an outer surface towards an inner surface of the inner sheath and along a portion of a length of the inner sheath, the axial slit having a proximal end positioned distal to the proximal end region of the inner sheath and a distal end positioned proximal to the distal end region of the inner sheath;

wherein the distal end region of the inner sheath is proximal to the distal end region of the slant;

wherein the sliding element is configured to extend into the axial slit; and a solid lubricant disposed between the inner sheath and the outer sheath;

advancing the stent delivery system to the desired location;

proximally retracting the outer sheath independently of the inner sheath over a distal portion of the stent; and proximally retracting the outer sheath and the inner sheath simultaneously over a proximal portion of the sten.

7. The method of claim 6, wherein proximally retracting the outer sheath independently of the inner sheath comprises proximally retracting the outer sheath until the sliding element on the outer sheath engages a mating feature on the inner sheath.

8. The method of claim 7, wherein proximally retracting the outer sheath and the inner sheath simultaneously over a proximal portion of the stent comprises the sliding element pulling the inner sheath with the outer sheath.

* * * * *